United States Patent
Römisch et al.

(10) Patent No.: US 6,790,832 B2
(45) Date of Patent: Sep. 14, 2004

(54) PHARMACEUTICAL PREPARATION FOR THE TREATMENT OF INFLAMMATORY PROCESSES

(75) Inventors: Jürgen Römisch, Marburg (DE); Gerhard Dickneite, Marburg (DE); Peter Gronski, Marburg (DE); Bernhard Vohwinkel, Marburg (DE); Harald Stauss, Dautphetal (DE); Elaine Gray, London (GB); Pauline Sxouter, St. Albans (GB); Stephen Poole, London (GB)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 10/127,572

(22) Filed: Apr. 23, 2002

(65) Prior Publication Data

US 2002/0164323 A1 Nov. 7, 2002

Related U.S. Application Data

(62) Division of application No. 09/492,790, filed on Jan. 28, 2000, now Pat. No. 6,399,572.

(30) Foreign Application Priority Data

Jan. 28, 1999 (DE) .......................................... 99 101 808

(51) Int. Cl.[7] .............................................. A61K 38/00
(52) U.S. Cl. .......................................... 514/12; 514/825
(58) Field of Search .................................. 514/12, 825

(56) References Cited

U.S. PATENT DOCUMENTS 6,399,572 B1 * 6/2002 Romisch et al. .............. 514/12

FOREIGN PATENT DOCUMENTS

| CA | 2124161 | 11/1994 |
|---|---|---|
| EP | 0 629 406 A1 | 12/1994 |
| EP | 0 952 215 A2 | 10/1999 |

OTHER PUBLICATIONS

Bosslet, K. et al., "Two Component System For Treatment of Sepsis and Septic Shock—Contains Thrombin Inhibitor and Substance Affecting Formation, Liberation, Plasma and Tissue Levels and Receptor Binding of Cytokines," Derwent Abstract, (1995).

Ozoran, K. et al., "Plasma von Willebrand Factor, Tissue Plasminogen Activator, Plasminogen Activator Inhibitor, and Antithrombin III Level Behcet's Disease," *Scandinavian Journal of Rheumatology*, vol. 24, pp. 376–382, BIOSIS Abstract, (1995).

Gabazza, Esteban Cesar et al. "Correlation Between Clotting and Collagen Metabolism Markers in Rheumatoid Arthritis," *Thrombosis and Haemostasis*, vol. 71(2):199–202 (1994).

Jones, H.W. et al., "Inactivation of Antithombin III in Synovial Fluid From Patients With Rheumatoid Arthritis," *Annals of the Rheumatic Disease*, vol. 57:162–165, (1998).

Choi–Miura, Nam–Ho et al., "Purification And Characterization Of A Novel Hyaluronan–Binding Protein (PHBP) From Human Plasma: It Has Three EGF, A Kringle And A Serine Protease Domain, Similar to Hepatocyte Growth Factor Activator," *J. Biochem.*, vol. 119, (6): 1157–1165 (1996).

Okajima, K. et al., "The Anti–Inflammatory Properties of Antithrombin III: New Therapeutic Implications," *Seminars in Thrombosis and Hemostasis*, vol. 24, No. 1: 27–32 (1998).

Dickneite, G., "Preclinical Evaluation of Antithrombin III in Experimental Sepsis and DIC.," Abstract #1469, Poster Board Session: 141–III: 357A (1998).

Nielsen, J. Dalsgaard, "The effect of antithrombin on the systemic inflammatory response in disseminated intravascular coagulation," *Blood Coagulation and Fibrinolysis*, 9 (suppl 3): S11–S15 (1998).

Risberg, B., "Antithrombin: Facts and new hypotheses," *Blood Coagulation and Fibrinolysis*, 9 (suppl 3): S3–S6 (1998).

Okajima, K., "New therapeutic implications of antithrombin III replacement in disseminated intravascular coagulation and multiple organ failure," *Intensivmedizin und Norfallmedizin*, vol. 33(1): 5–11 (1996).

Mammen, E., M.D., "Antithrombin: Its Physiological Importance and Role in DIC," Seminars in *Thombosis and Hemostasis*, vol. 24, (1): 19–25 (1998).

* cited by examiner

Primary Examiner—Theodore J. Criares
(74) Attorney, Agent, or Firm—Finnegan, Henderson, Farabow, Garrett and Dunner, L.L.P.

(57) ABSTRACT

A pharmaceutical preparation is described while is useful for the treatment of inflammatory processes being accompanied by an increased distribution of cytokines and/or tissue factor in the human body, which preparation contains Antithrombin III as active ingredient.

6 Claims, No Drawings

PHARMACEUTICAL PREPARATION FOR THE TREATMENT OF INFLAMMATORY PROCESSES

This is a Division of application Ser. No. 09/492,790, filed Jan. 28, 2000, now U.S. Patent 6,399,572, which is incorporated herein by reference.

The present invention relates to a pharmaceutical preparation for the treatment of inflammatory processes.

Sepsis is one of the main causes of death in developed countries and is commonly associated with the consumptive coagulopathy disorder, disseminated intravascular coagulation (DIC). One of the most common causes of sepsis is gram-negative or gram-positive bacterial infection. Lipopolysaccharide (LPS) or endotoxin, a cell wall component of gram negative bacteria such as Neisseria meningitidis, causes the production of proinflammatory, pyrogenic cytokines such as tumor necrosis factor a (TNFa), interleukin-1 (IL-1), interleukin-6 (IL-6) and interleukin-8 (IL-8). The circulatory levels of IL-6 and IL-8 have been shown to positively correlate with the severity of disease. These proinflammatory cytokines induce the expression of procoagulant tissue factor on monocytes and endothelial cells, thereby activating the extrinsic coagulation pathway. LPS can also activate factor XII, the contact phase of the intrinsic coagulation pathway. Activation of the coagulation cascade frequently leads to DIC, which is characterised by a pronounced depletion of coagulation factors and inhibitors. The consequence of this decrease in coagulation inhibitors, such as Antithrombin III (AT III), is uncontrolled thrombin formation leading to fibrin deposition in the microvascular beds; the reduction in clotting factors and platelets results in bleading diathesis. Simultaneously, the fibrinolytic system is activated increasing the likelihood of haemorrhage. Patients with congenital or acquired AT III deficiency and neonates/young children who have immature vascular endothelial anticoagulant systems, and therefore low levels of the coagulation inhibitors such as Protein C, are much more susceptible to DIC in the course of septic shock. Hence down-regulation of proinflammatory cytokine would be a desirable treatment for sepsis induced DIC.

During DIC, there is a massive consumption of AT III, the major plasma coagulation inhibitor. This is confirmed by a common observation in patients with septic shock where the plasma AT III levels in non-survivors are significantly lower than in survivors, and this decrease is more marked in individuals with DIC associated with sepsis. The general consensus is that an AT III level of less than 60% of normal results in a 100% mortality rate. Apart from its inhibitory action on thrombin AT III also has potent inhibitory effects on other coagulation serine proteases including factors IXa, Xa, XIa and XIIa. The rationale for treatment of DIC patients with AT III concentrate is therefore to replace the consumed inhibitor, so that thrombin formation could be controlled.

The present invention relates to the anti-inflammatory properties of AT III concentrates which are distinct from its anti-thrombin and anti-clotting capability. In a series of experiments the mechanism by which AT III inhibits LPS induced coagulation related inflammatory events i.e. the expression of procoagulant tissue factor and cytokines has been investigated. Human whole blood, isolated mononuclear cells (MNCs) or human umbilical vascular endothelial cells (HUVECs), when stimulated with E. coli LPS, responded with a dose dependent increase in the secretion of IL-6 and cell surface expression of tissue factor. AT III dose dependently inhibited these responses to LPS. Two surprising aspects arise from this data. Firstly, AT III is a potent inhibitor of thrombin, factor Xa and other activated clotting factors, but it is not known to inhibit tissue factor activity or expression. Secondly, AT III, a serine protease, is not known to interact with the cytokine network, yet IL-6 production evoked by LPS in the presence of AT III was decreased. Therefore AT III is not acting purely as an anti-coagulant but may also affect the signalling mechanism for regulation of the proin-flammatory cytokines.

Subject of the invention is therefore the use of Antithrombin III for the manufacture of an anti-inflammatory pharmaceutical preparation. Such a pharmaceutical preparation inhibits the production of pro-inflammatory cytokines and of tissue factor and is useful for the treatment of a sepsis induced disseminated intravasal coagulation (DIC), especially if caused by lipopolysaccarides (LPS).

Another subject of invention is the use of AT III for the prophylaxis and treatment of vasculitis like the systemic-necrotizing type as the polyartheritis nodosa or the Churg-Strauss syndrome (allergic angiitis). Furthermore AT III can used to prevent/treat hypersensitive vasculitis, whether caused by external stimuli like the Schoenlein-Henoch purpura, serum sickness or infectious vasculitis. Vasculites induced by endogenous antigens during/after cancer or systemic diseases of the connective tissue are included as well as the immune-vasculitis like the Wegener's granulomatosis, Kawasaki disease, systemic lupus erythematodes, Behcet syndrome, thrombangitis obliterans, artheritis temporalis etc. Other autoimmune diseases like the rheumatoid arthritis are accompanied by inflammatory reactions, which are characterized for instance by the release of inflammatory cytokines like IL-6.

The following describes the anti-inflammatory properties of AT Ill.

Human umbilical vein endothelial cells or purified MNCs were stimulated with 0-10 ng/mg of LPS (E. coli 2nd International Standard for Endotoxin) for 4–6 hours, in the absence or presence of AT III. The cells were than spun and the supernatants were used for cytokine measurement, while the cells were washed and assayed for tissue factor activity. IL-6 and IL-8 were measured by specific ELISA while tissue factor production was determined by tissue factor specific functional chromogenic assay. Table 1, 2 and 3 show typical results observed in the three cellular systems. With increasing doses of AT III, 20–40 IU/ml in these experiments, there was a corresponding decrease in the production of TF, IL-6 and IL-8.

TABLE 1

%-inhibition of TF, IL-6 and IL-8 production by AT III,
in the presence of 1 ng/ml of LPS, in MNCs.

| | % Inhibition | | |
|---|---|---|---|
| AT III (IU/ml) | 20 | 30 | 40 |
| TF | 18.1 | 36.6 | 58.1 |
| LIL-6 | 49.0 | 72.5 | 89.2 |
| IL-8 | −19.4* | −7.6* | 8.8 |

*denotes potentiation

In isolation MNC systems, AT III inhibited the production of both tissue factor and IL-6 in a dose dependent manner. At 20 and 30 IU/ml, AT III potentiated the expression of IL-8, buy a reduction of 8,8% was observed at 40 IU/ml.

TABLE 2

%-inhibition of TF, IL-6 and IL-8 production by AT III,
in the presence of 1 ng/ml of LPS, in HUVEC.

| | % Inhibition | | |
|---|---|---|---|
| AT III (IU/ml) | 20 | 30 | 40 |
| TF | 7.3 | 14.3 | 36.3 |
| IL-6 | 18.5 | 32.7 | 69.0 |
| IL-8 | −18.1* | 4.3 | 21.3 |

*denotes potentiation

As found with MNC, AT III also inhibited expression of tissue factor, IL-6 and IL-8 by LPS stimulated HUVEC.

TABLE 3

%-inhibition of TF, IL-8 production by AT III,
in the presence of 10 ng/mg of LPS, in whole blood.

| | % Inhibition | | |
|---|---|---|---|
| AT III (IU/ml) | 20 | 30 | 40 |
| TF | 54.42 | 88.14 | 92.54 |
| IL-6 | 100 | 100 | 100 |

*denotes potentiation

As the above results illustrate, in whole blood, AT III inhibited the production of tissue factor and IL-6 to a greater extent when compared to MNCs or HUVECs; with−93% inhibition of TF at 40 IU/ml AT III.

These results indicate that, apart from the inhibition of thrombin and other activated clotting factors, AT III may have a role in modulating the levels of proinflammatory cytokines. Hence, AT III concentrates could be used clinically to down-regulate the expression and production of pro-inflammatory cytokines (TNFa, IL-1, IL-6, IL-8) and procoagulant tissue factor, induced by bacterial LPS, as in the case of sepsis induced DIC.

Based on the above mentioned findings a pharmaceutical preparation containing AT III has been developed for the treatment of inflammatory processes which are characterized by an increased distribution of cytokines and/or tissue factor in the human body. Such preparation may be administered by injection or infusion. Normally it will be offered for sale as a dry substance in a vial with a piercable cap together with a separately packed solvent. The amount of the active ingredient for each adminisration is normally between 250 and 2500 IU. As a solvent water pro injection, Ringer lacyate solution or an isotonic water solution may be used which may contain citrate, sodium hydrogenphosphat, one or several amino acids, human albumin or an infusion solution containing a plasma replacement.

What is claimed is:

1. A method for the treatment of rheumatoid arthritis comprising administration of a pharmaceutical composition comprising Antithrombin III (AT III).

2. The method according to claim 1, wherein administration is by injection or infusion.

3. The method according to claim 1, wherein the pharmaceutical composition also comprises at least one of the following: citrate, glucose, sodium hydrogenphosphate, at least one amino acid, human albumin and a plasma replacement.

4. A method for the prevention of rheumatoid arthritis comprising administering, to a patient in need thereof, a pharmaceutical composition comprising Antithrombin III (AT III).

5. The method according to claim 4, wherein administration is by injection or infusion.

6. The method according to claim 4, wherein the pharmaceutical composition also comprises at least one of the following: citrate, glucose, sodium hydrogenphosphate, at least one amino acid, human albumin and a plasma replacement.

* * * * *